US00PP37217P2

(12) United States Plant Patent
Boxriker

(10) Patent No.: US PP37,217 P2
(45) Date of Patent: Jan. 13, 2026

(54) ***DAHLIA* PLANT NAMED 'KLEDH24725'**

(50) Latin Name: ***Dahlia* sp.**
Varietal Denomination: KLEDH24725

(71) Applicant: KLEMM + SOHN GMBH & CO. KG, Stuttgart (DE)

(72) Inventor: Maike Boxriker, Stuttgart (DE)

(73) Assignee: Klemm + Sohn Gmbh & Co. KG, Stuttgart (DE)

( * ) Notice: Subject to any disclaimer, the term of this patent is extended or adjusted under 35 U.S.C. 154(b) by 0 days.

(21) Appl. No.: 19/307,947

(22) Filed: Aug. 22, 2025

(51) Int. Cl.
*A01H 5/02* (2018.01)

(52) U.S. Cl.
USPC ..... Plt./321

(58) Field of Classification Search
USPC ..... Plt./321
CPC ..... A01H 6/144; A01H 5/02
See application file for complete search history.

*Primary Examiner* — Keith O. Robinson
(74) *Attorney, Agent, or Firm* — Weatherly IP Solutions, LLC; Karen P. Bechtold; James Weatherly

(57) ABSTRACT

A new *Dahlia* plant designated 'KLEDH24725' particularly distinguished by light pink and white flowers with varying color proportions, and a double composite head inflorescence held above the foliage as described herein.

1 Drawing Sheet

Genus and species: *Dahlia* sp.
Variety denomination: 'KLEDH24725'.

BACKGROUND

The present invention comprises a new and distinct variety of *Dahlia*, botanically known as *Dahlia* sp., and hereinafter referred to by the variety name 'KLEDH24725'. 'KLEDH24725' originated from an open pollination with the female *Dahlia* 'PH-2018-5130' (unpatented) and an unknown male *Dahlia* plant in Summer 2020 in Latina, Italy. In March 2021, a seedling was selected and named 'KLEDH24725'. 'KLEDH24725' was first vegetatively propagated by vegetative cuttings in May 2021 in Latina, Italy. 'KLEDH24725' was found to reproduce true to type in successive generations of asexual propagation.

SUMMARY

The following are the most outstanding and distinguishing characteristics of 'KLEDH24725' when grown under normal horticultural practices in Stuttgart, Germany and Latina, Italy.

1. Light pink and white flowers with varying color proportions, and
2. A double composite head inflorescence held above the foliage.

DESCRIPTION OF THE PHOTOGRAPH

This new *Dahlia* plant is illustrated by the accompanying photograph of the plant approximately fourteen weeks old and grown in a greenhouse in Stuttgart, Germany. The photograph shows the whole plant, including the inflorescences and foliage and buds and was taken in May 2024 in Stuttgart, Germany. The colors shown are as true as can be reasonably obtained by conventional photographic procedures.

DESCRIPTION OF 'KLEDH24725'

The following detailed descriptions set forth the distinctive characteristics of 'KLEDH24725'. The data which define these characteristics were collected from asexual reproductions carried out in Latina, Italy. Data was collected on 16-week-old plants grown in a greenhouse in Latina, Italy. Color references are to The R.H.S. Colour Chart of The Royal Horticultural Society of London (R.H.S.), 5$^{th}$ edition (2007).

Classification:
- *Family*.—Asteraceae.
- *Botanical*.—*Dahlia* sp.
- *Designation*.—'KLEDH24725'.

Parentage:
- *Female parent*.—'PH-2018-5130' (unpatented).
- *Male parent*.—Unknown male parent.

Propagation:
- *Type*.—Vegetative terminal cuttings.
- *Time to produce a rooted young plant*.—3 to 4 weeks.
- *Root description*.—RHS N155C in color, fine.
- *Rooting habit*.—Freely branching and moderately dense.

Plant description:
- *Plant and growth habit*.—Semi-spreading.
- *Plant height*.—To the top of foliar plane: 24.0 cm. Including inflorescence: 34.0 cm.
- *Plant diameter*.—35.0 cm.

Lateral branches:
- *Length*.—Up to the last pair of leaves: 19.0 cm. Including inflorescence: 25.0 cm.
- *Diameter*.—0.4 cm.
- *Internode length*.—Up to 6.5 cm.
- *Color*.—Close to RHS N77A at the front and RHS 144A at the back.

Foliage description:
- *Arrangement*.—Opposite, simple to pinnate.
- *Length*.—12.0 cm.
- *Width*.—8.5 cm.
- *Shape*.—Pinnate.
- *Apex*.—Acute.
- *Base*.—Acute.
- *Margin*.—Irregularly serrate.
- *Venation pattern*.—Pinnate.

*Venation color*.—RHS 146A.
*Texture*.—Upper and lower surface: Slightly hairy on the edges, slightly rugose and glossy.
*Color*.—Immature: Upper surface: RHS N189A. Lower surface: RHS 191A. Mature: Upper surface: RHS N137A. Lower surface: RHS 191B.

Petioles:
*Length*.—2.5 cm.
*Diameter*.—0.4 cm.
*Texture*.—Upper surface: Smooth. Lower surface: Smooth.
*Color*.—Upper surface: RHS 148C. Lower surface: RHS 195A.

Inflorescence description:
*Appearance and arrangement*.—Composite head inflorescence, double, held above the foliage.
*Fragrance*.—Absent.
*Time to flower*.—About 9.5 weeks after potting in greenhouse conditions.
*Post-production longevity*.—Plants flower continuously from spring through autumn.

Inflorescence bud:
*Height*.—1.5 cm.
*Diameter*.—1.7 cm.
*Shape*.—Globular.
*Color*.—RHS 143A at the base and RHS 144B toward the tips.

Inflorescence size:
*Diameter*.—6.5 cm.
*Depth (height)*.—2.0 cm.
*Disc diameter*.—Not visible.
*Receptacle height*.—0.5 cm.
*Receptacle diameter*.—1.5 cm.
*Receptacle color*.—RHS 137C.

Ray florets:
*Quantity per inflorescence*.—Approximately 100.
*Length*.—3.0 cm.
*Width*.—1.5 cm.
*Shape*.—Elliptic.
*Apex*.—Pointed.
*Base*.—Fused in a tube.
*Margin*.—Entire.
*Aspect*.—Keeled.
*Texture*.—Upper surface: Smooth. Lower surface: Smooth.
*Color*.—Immature and Mature: Upper surface: RHS N155B and RHS 72D, proportion of the colors changing between majority of inflorescence and marginal zone during the season and in different environmental conditions. Lower surface: RHS N155B and RHS 72D, proportion of the colors changing between majority of inflorescence and marginal zone during the season and in different environmental conditions.

Disc florets:
*Quantity per inflorescence*.—Approximately 34.
*Length*.—1.3 cm.
*Diameter*.—0.2 cm.
*Shape*.—Tubular.
*Texture*.—Inner surface: Smooth. Outer surface: Smooth.
*Color*.—Immature: Inner surface: RHS close to 1B. Outer surface: RHS close to 1B. Mature: Inner surface: RHS close to 2B. Outer surface: RHS close to 2B.

Phyllaries:
*Quantity per inflorescence*.—7 at the external whorl, 10 in the internal whorl.
*Length*.—External: 1.5 cm. Internal: 1.8 cm.
*Width*.—External: 0.4 cm. Internal: 0.6 cm.
*Shape*.—Lanceolate to spatulate.
*Apex*.—Broadly acute.
*Base*.—External: Attenuate. Internal: Fused.
*Margin*.—Entire.
*Texture*.—Upper surface: Smooth and slightly glossy. Lower surface: Smooth and slightly glossy.
*Color*.—Upper surface: External whorl: RHS N137B. Internal whorl: RHS 143A at the base to RHS 145A at the tips. Lower surface: External whorl: RHS N137B. Internal whorl: RHS 143A at the base to RHS 145B at the tips.

Peduncles:
*Length, terminal peduncle*.—9.5 cm.
*Length, axillary peduncle*.—6.5 cm.
*Diameter*.—0.3 cm.
*Texture*.—Smooth.
*Color*.—RHS 200A.

Reproductive organs:
*Androecium*.—Quantity per floret: 5 stamens with fused anthers. Filament length: 0.2 cm. Filament color: RHS 150D. Anther shape: Oblong. Anther length: 0.3 cm. Anther color: RHS 17A. Pollen amount: Abundant. Pollen color: RHS 17B.
*Gynoecium*.—Quantity per floret: 1. Pistil length: 1.3 cm. Style length: 1.0 cm. Style color: RHS 145D. Stigma shape: Bipartite. Stigma color: RHS 22A. Ovary color: RHS 145A/145B.

Fruit and seed set: Not yet observed.

Disease and pest/insect resistance: No disease resistance observed.

COMPARISON OF 'KLEDH24725' WITH PARENTAL LINE AND KNOWN VARIETY

'KLEDH24725' is distinguished from the parent as described in Table 1.

TABLE 1

Comparison with Parental Line

| Trait | Variety 'KLEDH24725' | Female parent 'PH-2018-5130' |
|---|---|---|
| Flower color | Light pink and white with varying color proportions | Purple-pink |

'KLEDH24725' can be compared to the commercial *Dahlia* variety 'KLEDH24716' (unpatented). Differences between the varieties are described in Table 2.

TABLE 2

Comparison with Similar Variety

| Trait | Variety 'KLEDH24725" | Commercial line 'KLEDH24716' (unpatented) |
|---|---|---|
| Flower color | Light pink and white with varying color proportions | Purple magenta with white tips |

I claim:

1. A new and distinct variety of *Dahlia* plant designated 'KLEDH24725' as shown and described herein.

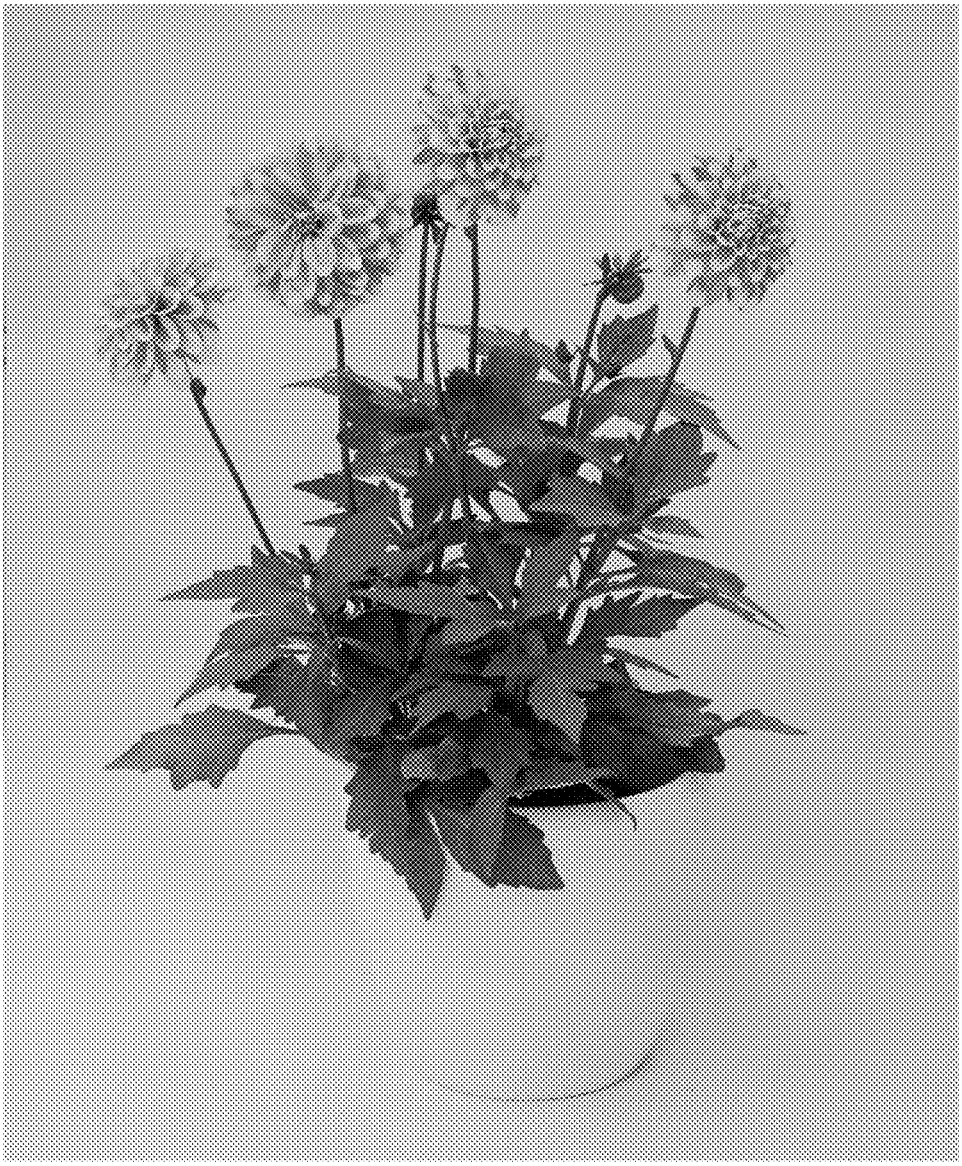

* * * * *